(12) United States Patent
Shuros et al.

(10) Patent No.: US 9,616,228 B2
(45) Date of Patent: *Apr. 11, 2017

(54) DEVICE AND METHOD FOR MODULATING RENAL FUNCTION

(71) Applicant: Cardiac Pacemakers, Inc., St. Paul, MN (US)

(72) Inventors: Allan C. Shuros, St. Paul, MN (US); M. Jason Brooke, Woodstock, MD (US); Tasneem Poonawala, Eagan, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 891 days.

This patent is subject to a terminal disclaimer.

(21) Appl. No.: 13/867,552

(22) Filed: Apr. 22, 2013

(65) Prior Publication Data

US 2013/0237954 A1    Sep. 12, 2013

Related U.S. Application Data

(63) Continuation of application No. 12/825,174, filed on Jun. 28, 2010, now Pat. No. 8,425,454, which is a continuation of application No. 11/567,907, filed on Dec. 7, 2006, now Pat. No. 7,744,618.

(51) Int. Cl.
*A61N 1/36* (2006.01)
*A61M 25/00* (2006.01)
*A61N 1/05* (2006.01)

(52) U.S. Cl.
CPC ........... *A61N 1/3606* (2013.01); *A61M 25/00* (2013.01); *A61N 1/36007* (2013.01); *A61N 1/36135* (2013.01); *A61N 1/05* (2013.01)

(58) Field of Classification Search
CPC .............. A61N 1/3606; A61N 1/36135; A61N 1/36007; A61N 1/05; A61M 25/00
USPC ...... 606/112, 194, 192, 191; 607/60; 600/16
See application file for complete search history.

(56) References Cited

U.S. PATENT DOCUMENTS

| | | |
|---|---|---|
| 5,231,988 A | 8/1993 | Wernicke et al. |
| 5,902,336 A | 5/1999 | Mishkin |
| 6,296,615 B1 | 10/2001 | Brockway et al. |
| 6,512,949 B1 | 1/2003 | Combs et al. |
| 7,539,533 B2 | 5/2009 | Tran |
| 7,744,618 B2 | 6/2010 | Allan et al. |
| 8,425,454 B2 * | 4/2013 | Shuros ............... A61N 1/36007 604/96.01 |

(Continued)

OTHER PUBLICATIONS

"U.S. Appl. No. 11/567,907, Non-Final Office Action mailed Feb. 18, 2009", 17 pgs.

(Continued)

*Primary Examiner* — Manuel Mendez
(74) *Attorney, Agent, or Firm* — Schwegman Lundberg & Woessner, P.A.

(57) ABSTRACT

Renal function may be modulated by an implantable device having one or more leads or catheters disposed near the kidney via the lymphatic system. In one embodiment, lymphatic drainage from the kidney is modulated to increase or decrease tubular reabsorption of salt and water. The renal function modulation therapy may be delivered in an open-loop or closed-loop fashion, with the latter dependent upon a physiological variable such as blood pressure or cardiac output.

20 Claims, 9 Drawing Sheets

(56) References Cited

U.S. PATENT DOCUMENTS

| | | |
|---|---|---|
| 2003/0060848 A1 | 3/2003 | Kieval et al. |
| 2003/0171640 A1 | 9/2003 | Canedo |
| 2003/0199806 A1 | 10/2003 | Kieval |
| 2003/0216792 A1 | 11/2003 | Levin et al. |
| 2004/0059276 A1 | 3/2004 | Maguire et al. |
| 2004/0204744 A1 | 10/2004 | Penner et al. |
| 2005/0288730 A1 | 12/2005 | Deem et al. |
| 2008/0140000 A1 | 6/2008 | Shuros et al. |
| 2010/0268194 A1 | 10/2010 | Shuros et al. |

OTHER PUBLICATIONS

"U.S. Appl. No. 11/567,907, Final Office Action mailed Sep. 21, 2009", 11 Pgs.

"U.S. Appl. No. 11/567,907, Notice of Allowance mailed Feb. 22, 2010", 7.

"U.S. Appl. No. 11/567,907, Response filed Nov. 23, 2009 to Final Office Action mailed Sep. 21, 2009", 5 pgs.

"U.S. Appl. No. 11/567,907, Response filed May 18, 2009 to Non Final Office Action mailed Feb. 18, 2009", 9 pgs.

"U.S. Appl. No. 12/825,174, Ex Parte Quayle Action mailed Oct. 5, 2012", 6 pgs.

"U.S. Appl. No. 12/825,174, Notice of Allowance mailed Dec. 24, 2012", 7 pgs.

"U.S. Appl. No. 12/825,174, Response filed Dec. 5, 2012 to Ex Parte Quayle Action mailed Oct. 5, 2012", 7 pgs.

"U.S. Appl. No. 12/825,174, Response filed Sep. 13, 2012 to Restriction Requirement mailed Aug. 13, 2012", 9 pgs.

"U.S. Appl. No. 12/825,174, Restriction Requirement mailed Aug. 13, 2012", 6 pgs.

\* cited by examiner

DEVICE AND METHOD FOR MODULATING RENAL FUNCTION

CLAIM OR PRIORITY

This application is a continuation of U.S. application Ser. No. 12/825,174, filed Jun. 28, 2010, which is a continuation of U.S. application Ser. No. 11/567,907, filed Dec. 7, 2006, now issued as U.S. Pat. No. 7,744,618, each of which is hereby incorporated by reference in its entirety.

This application is related to U.S. patent application Ser. No. 11/422,414, filed on Jun. 6, 2006, now issued as U.S. Pat. No. 7,894,906, Ser. No. 11/422,417, filed on Jun. 6, 2006, now issued as U.S. Pat. No. 7,526,337, Ser. No. 11/422,418 filed on Jun. 6, 2006, now issued as U.S. Pat. No. 7,734,341, Ser. No. 11/559,131, filed on Nov. 13, 2006, abandoned, Ser. No. 11/422,421, filed on Jun. 6, 2006, abandoned, and Ser. No. 11/539,301, filed on Oct. 6, 2006, now issued as U.S. Pat. No. 7,664,548, all hereby incorporated by reference.

FIELD OF THE INVENTION

This patent application pertains to methods and apparatus for the treatment of disease.

BACKGROUND

The primary functions of the kidneys are to rid the body of metabolic and ingested waste products and to maintain the volume and composition of body fluids. The kidneys perform these functions by filtering the blood through the glomerular capillaries into the renal tubules. As the filtrate passes down the tubules, its composition is altered as substances are selectively reabsorbed back into the non-filtered blood in the peritubular capillaries that surround the tubules. Substances may also be selectively secreted from the tubules into the peritubular capillary blood. After these processes of tubular reabsorption and tubular secretion have taken place, the resulting filtrate is excreted as urine.

The maintenance of a constant extracellular fluid (ECF) volume by the kidneys is accomplished by various neural, hormonal, and intrinsic homeostatic mechanisms that control the rate at which blood is filtered by the glomeruli, referred to as the glomerular filtration rate (GFR), and the extent to which sodium and water are reabsorbed from the filtrate into the peritubular capillary blood. The body defends against changes in both arterial pressure and ECF volume by controlling GFR and the tubular reabsorption of sodium and water in response to changes in arterial blood pressure. The kidneys then produce a volume of urine as appropriate to cause the body to excrete or retain water. One of these homeostatic mechanisms is the renin-angiotensin-aldosterone system (RAAS). A decrease in arterial blood pressure (and/or a decrease in plasma osmolarity) causes juxtaglomerular cells in the kidney to release renin into the blood. Renin is an enzyme that converts a circulating protein called angiotensinogen into angiotensin I, the latter then being enzymatically converted into angiotensin II. Angiotensin II is a very potent vasoconstrictor that constricts blood vessels in many areas of the body to raise peripheral resistance and arterial pressure. Angiotensin II also causes the kidneys to retain sodium and water in several ways that include: 1) causing the adrenal glands to secrete aldosterone, which then acts on the renal tubules to increase sodium and water reabsorption, 2) causing constriction of renal arterioles to diminish renal blood flow and GFR, and 3) acting directly on the renal tubules to increase tubular reabsorption of sodium and water. The opposite effects occur when blood pressure rises.

Another homeostatic mechanism is pressure natriuresis, which refers to the intrinsic response of the kidneys when renal arterial pressure increases to increase urinary excretion of sodium and water. When renal arterial pressure rises, renal blood flow and GFR increase which increases the amount of tubular fluid. Also, increased renal arterial pressure raises the hydrostatic pressure in the peritubular capillaries and the renal interstitium which reduces the reabsorption of sodium and water from the tubules. Both of these effects thus result in an increased volume of urine when renal arterial pressure rises and vice-versa.

The kidneys also receive extensive sympathetic innervation and respond to changes in sympathetic activity. Baroreceptors, such as those in the aortic arch and carotid sinus, activate the sympathetic nervous system in response to a decrease in arterial blood pressure. Increased sympathetic activity decreases sodium and water excretion in several ways that include: 1) constricting the renal arterioles to decrease renal blood flow and GFR, 2) acting on the renal tubules to increase reabsorption of sodium and water, and 3) stimulating the release of renin.

The kidneys normally act so as to maintain both arterial blood pressure and ECF volume within desired normal ranges. In certain pathological situations, however, the homeostatic mechanisms discussed above do not respond in an appropriate manner to maintain blood pressure and/or ECF volume within normal ranges. For example, the intrinsic autoregulation of GFR by the kidney is often impaired in kidney disease causing a greater than normal pressure natriuresis. In some patients with hypertension, on the other hand, the pressure natriuresis mechanism may be impaired so that the kidneys do not excrete adequate amounts of salt and water unless arterial pressure becomes abnormally high. Hypertension may also result from the renal response to increased sympathetic activity.

Another situation in which the homeostatic mechanisms of the kidneys may not respond in an optimal manner is during heart failure (HF), which refers to a clinical syndrome in which an abnormality of cardiac function causes a below normal cardiac output that can fall below a level adequate to meet the metabolic demand of peripheral tissues. HF can be due to a variety of etiologies with ischemic heart disease being the most common. When heart failure occurs acutely, such as from a myocardial infarction (MI), sympathetic circulatory reflexes are activated that both increase the contractility of the heart and constrict the vasculature as the body tries to defend against the drop in blood pressure. Venous constriction, along with the reduction in the heart's ability to pump blood out of the venous and pulmonary systems (so-called backward failure), causes an increase in the diastolic filling pressure of the ventricles. This increase in preload (i.e., the degree to which the ventricles are stretched by the volume of blood in the ventricles at the end of diastole) causes an increase in stroke volume during systole, a phenomena known as the Frank-Starling principle. If the heart failure is not too severe, this compensation is enough to sustain the patient at a reduced activity level. When moderate heart failure persists, other compensatory mechanisms come into play that characterize the chronic stage of heart failure. The most important of these is the depressing effect of a low cardiac output on renal function due to decreased renal perfusion, which causes a reduction in salt and water excretion by the pressure natriuresis mechanism. The increased sympathetic activity in response to low blood pressure and/or cardiac output may also depress renal function still further. The increased fluid retention by the kidneys results in an increased blood volume and further increased venous return to the heart, thus increasing the heart's preload. A state of compensated heart failure results when the factors that cause increased diastolic filling pressure are able to maintain cardiac output at a normal level even while the pumping ability of the heart is compromised. If cardiac function worsens or increased cardiac output is required due to increased activity or illness, however, the compensation may not be able to maintain cardiac output at a level sufficient to maintain normal renal function. Fluid then continues to be retained by kidneys, causing the progressive peripheral and pulmonary edema that characterizes overt congestive heart failure. Diastolic filling pressure also becomes further elevated which causes the heart to become so dilated and edematous that its pumping function deteriorates even more. This condition, in which the heart failure continues to worsen while excess fluid accumulates in the lungs and extremities, is decompensated heart failure. It can be detected clinically, principally from the resulting pulmonary congestion and dyspnea, and can lead to rapid death unless appropriate therapy is instituted.

Even if acute decompensation does not occur, persistent heart failure and accompanying fluid retention by the kidneys may result in a complex remodeling process of the ventricles that involves structural, biochemical, neurohormonal, and electrophysiologic factors. When the ventricles are stretched due to the increased preload over a period of time, the ventricles become dilated. As the heart begins to dilate, afferent baroreceptor and cardiopulmonary receptor signals are sent to the vasomotor central nervous system control center, which responds with hormonal secretion and sympathetic discharge. It is the combination of hemodynamic, sympathetic nervous system and hormonal alterations (such as presence or absence of angiotensin converting enzyme (ACE) activity) that ultimately account for the deleterious alterations in cell structure involved in ventricular remodeling. The sustained stresses caused by the increased loading induce apoptosis (i.e., programmed cell death) of cardiac muscle cells and eventual wall thinning which causes further deterioration in cardiac function. It has been shown that the extent of ventricular remodeling is positively correlated with increased mortality in post-MI and heart failure patients.

Modulation of renal function to improve the situations described above can be performed by pharmacological means. For example, in the treatment of hypertension, vasodilators can be used to increase renal blood flow, and diuretic drugs can be used to decrease the tubular reabsorption of salt and water. Such pharmacological agents are not always effective, however, and they are not without significant side effects.

DETAILED DESCRIPTION

Described herein are methods and devices for modulating renal function in those situations where the normal homeostatic mechanisms for regulating fluid balance do not produce optimal results. As described in greater detail below, renal function modulation therapy may be delivered by an implantable device that utilizes one or more leads or catheters that may be routed via the lymphatic system to an appropriate site for affecting renal function with a particular kind of therapy. Such therapies may include one or more of the following: blocking renal lymphatic flow, augmenting renal lymphatic flow, delivery of a drug directly to the kidney by retrograde infusion through a lymphatic vessel, and inhibition or stimulation of the renal nerve or other sites affecting renal sympathetic stimulation. Renal function modulation therapy may be used in the treatment of, for example, chronic heart failure, acute decompensated heart failure, acute MI, hypertension, and renal dysfunction.

Figure 1:
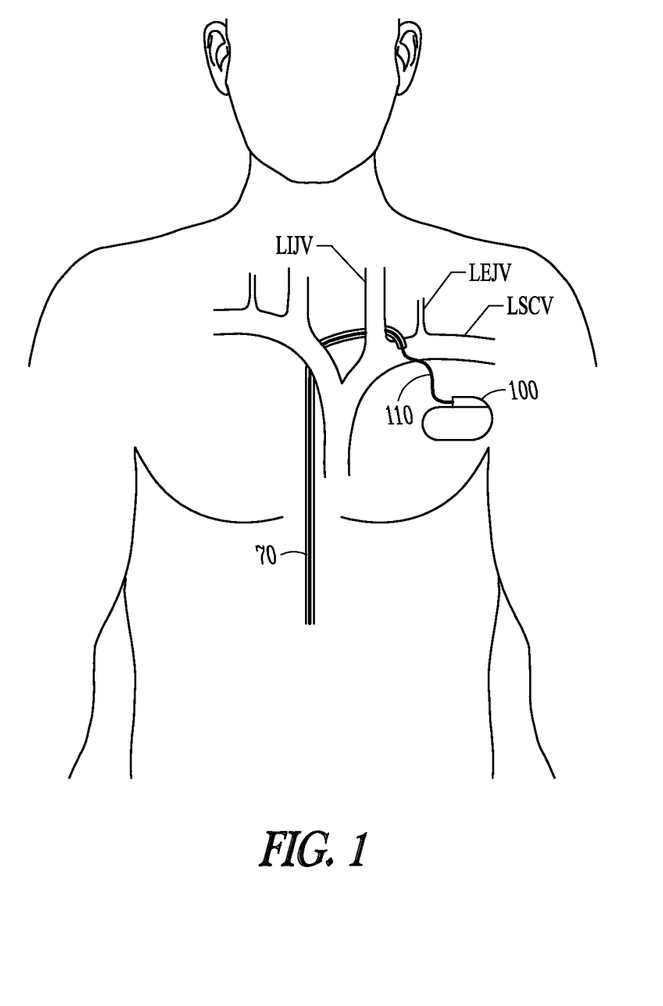
FIG. 1 shows the physical placement an exemplary implantable device for delivering renal function modulation therapy.

FIG. 1 shows an exemplary implantable device 100 for delivering renal function modulation therapy having one or more leads or catheters 110 that are disposed near a renal therapy target site via the lymphatic system. The implantable device 100 may be placed subcutaneously or submuscularly in a patient's chest, similar to a cardiac pacemaker, or other convenient location. The implantable device 100 includes a hermetically sealed housing for containing circuitry and other components that are used to deliver therapy such as a power supply, monitoring circuitry, therapy circuitry, and a programmable electronic controller for controlling the operation of the device. A header is mounted on the housing for receiving the one or more leads or catheters 110 which are connected to the functional components within the housing. FIG. 1 also illustrates relevant portions of the lymphatic and venous system including portions of the thoracic duct TD, left subclavian vein LSCV, left external jugular vein LEJV, and left internal jugular vein LIJV. The thoracic duct connects to the left subclavian vein at the juncture of subclavian vein and the left internal jugular vein. Lymphatic fluid from the kidneys and the rest of the lower body flows up the thoracic duct and empties into the left subclavian vein. FIG. 1 shows that the one or more leads or catheters 110 from the implantable device are introduced into the venous system via the subclavian vein and from there into the thoracic duct. From the thoracic duct, the lead/catheter 100 may then be advanced further to a renal lymphatic vessel using techniques as described in U.S. application Ser. No. 11/422,423, filed on Jun. 6, 2006, hereby incorporated by reference. In other embodiments, the leads or catheters 110 may be replaced with a wireless communications link between the implantable device 100 and a satellite actuating unit for delivering the renal function modulation therapy. In an embodiment where the implantable device also functions as a cardiac device, one or more leads for delivering electrical stimulation and/or detecting cardiac electrical activity may also be advanced from the subclavian vein into the heart in the conventional manner. An implantable device for delivering renal function modulation therapy as discussed herein may also be combined with a cardiac device configured to deliver bradycardia pacing, anti-tachyarrhythmia therapy, cardiac resynchronization pacing, and/or pre-excitation pacing for redistributing myocardial wall stress.

Figure 2A:
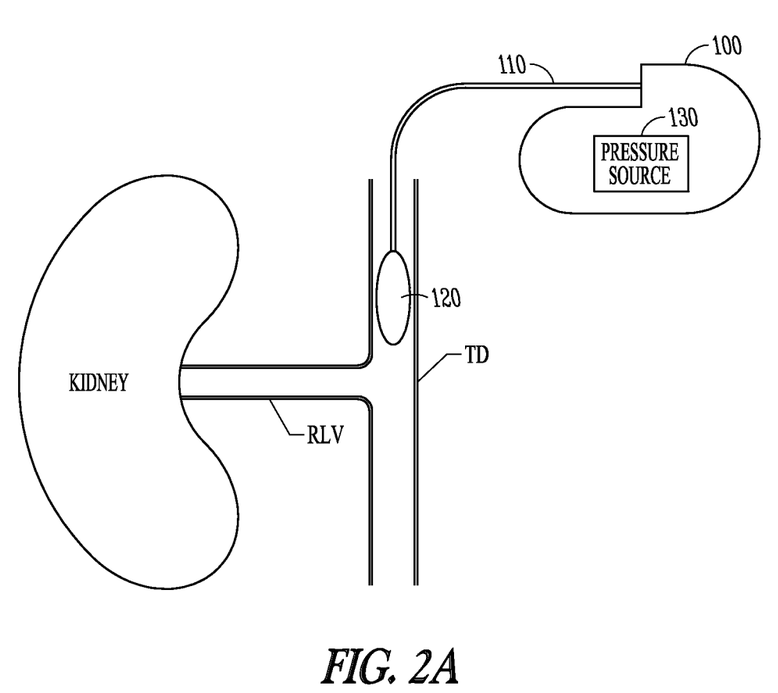
FIGS. 2A through 2C show embodiments of a device for delivering renal function modulation therapy by obstructing lymphatic flow from kidney.
Figure 2B:
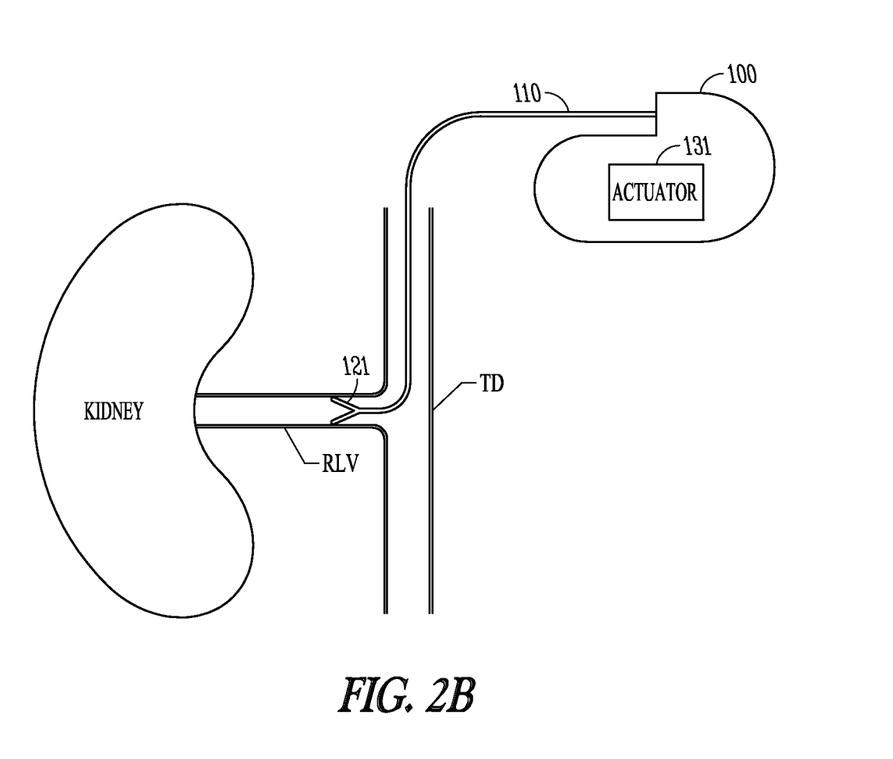
Figure 2C:
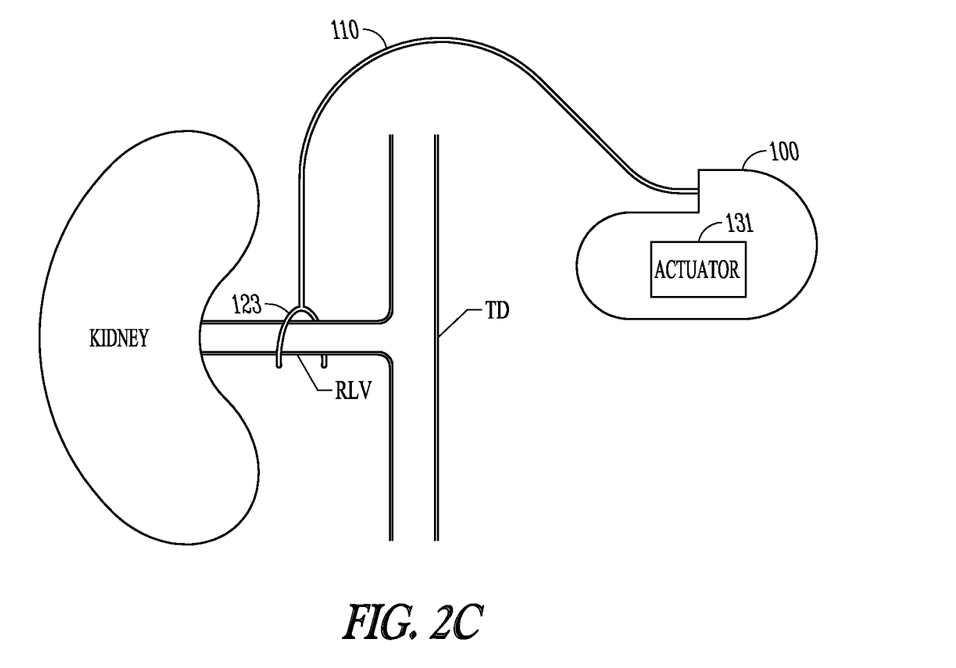

FIGS. 2A through 2C show embodiments of the device 100 that are configured for delivering renal function modulation therapy by obstructing lymphatic flow from kidney into the thoracic duct. When renal lymphatic flow is obstructed, the concentration of proteins in the renal interstitium that are normally carried away by the lymphatic system increases. This increased protein concentration causes an increase in interstitial colloid osmotic pressure that hinders reabsorption of salt and water from the tubular fluid into the peritubular capillaries. The result is increased excretion of salt and water. In order to obstruct renal lymphatic flow in a controllable manner, the catheter 110 shown in FIG. 1 may incorporate an occluding structure at its distal end that is operable by the implantable device 100. For example, in the embodiment shown in FIG. 2A, an inflatable balloon 120 is incorporated into the catheter 110 and disposed in the renal lymphatic vessel RLV or thoracic duct itself (preferably in the proximal thoracic duct just in front of the renal lymph vessel). The balloon 120 may be inflated by a pressurized fluid source 130 operable by a controller in the implantable device 100 to cause a desired degree of lymphatic flow obstruction. Other embodiments could use mechanically operated structures that are controllably expanded within the lymphatic vessel lumen to obstruct lymphatic flow. In the embodiment shown in FIG. 2B, for example, the lead 110 is connected to a mechanical valve 121 that is operated by a valve actuator 131 to either allow or restrict flow within the lymphatic vessel. Other embodiments, rather than using a balloon or other occluding structure within the lymphatic vessel to restrict flow, use a cuff or pinching structure implanted around the lymphatic vessel to constrict flow. FIG. 2C shows an embodiment in which a cuff 123 is operated by an actuator 131 in the implantable device 100 to control flow within the lymphatic vessel. The cuff 123 may be, for example, an inflatable or mechanically operated structure for controllably constricting the diameter of the lymphatic vessel. The cuff 123 may be connected to the implantable device 100 by a lead or catheter 110 as shown in FIG. 2C or may be incorporated into an implantable satellite actuating unit that communicates wirelessly with the implantable device 100. A sensor (for example, a blood pressure or cardiac output sensor) may be provided to enable closed-loop control of renal function modulation therapy in these and the other embodiments discussed below with reference to FIGS. 3-5. Alternatively, the therapies may be delivered in open-loop fashion by, for example, transmitting a command to the implantable device via telemetry.

Figure 3:
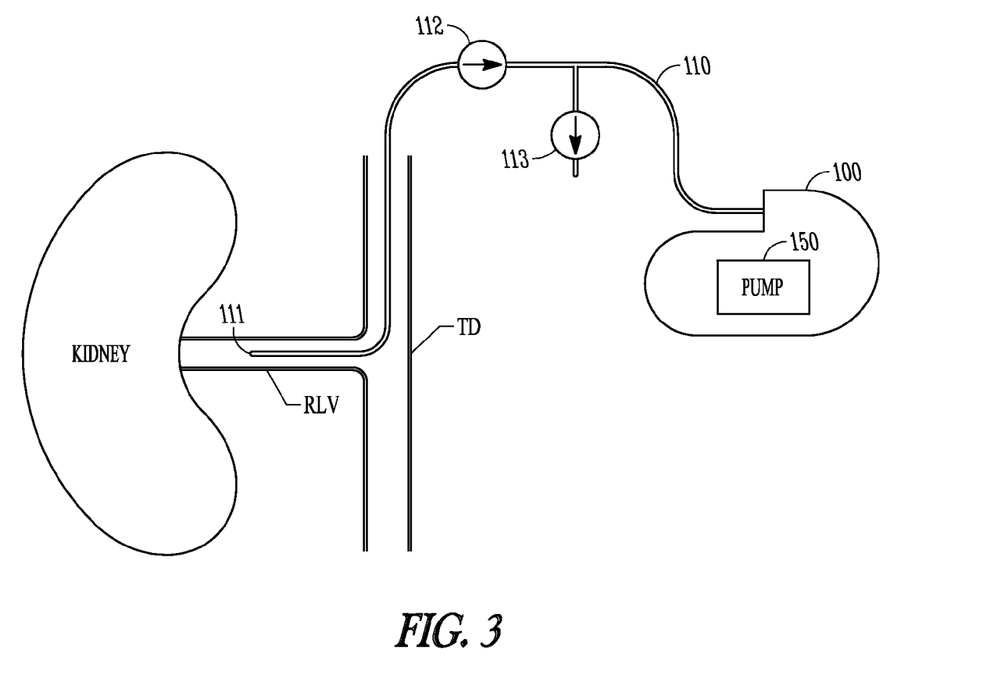
FIG. 3 shows an embodiment for delivering renal function modulation therapy by augmenting renal lymphatic flow.

FIG. 3 shows another embodiment for delivering renal function modulation therapy by affecting renal lymphatic flow. In this embodiment, the catheter 110 has a lumen that communicates from an opening 111 at the distal end of the catheter to a pumping mechanism 150 in the implantable device 100. The implantable device is then able to controllably augment renal lymphatic flow by actively pumping lymphatic fluid from the kidney. Such augmentation of lymphatic flow acts to increase the retention of salt and water by the mechanism discussed above. In the embodiment shown, unidirectional valves 112 and 113 are incorporated into the catheter 110 to allow lymphatic fluid to be pumped from the renal lymphatic vessel to the venous system.

Figure 4:
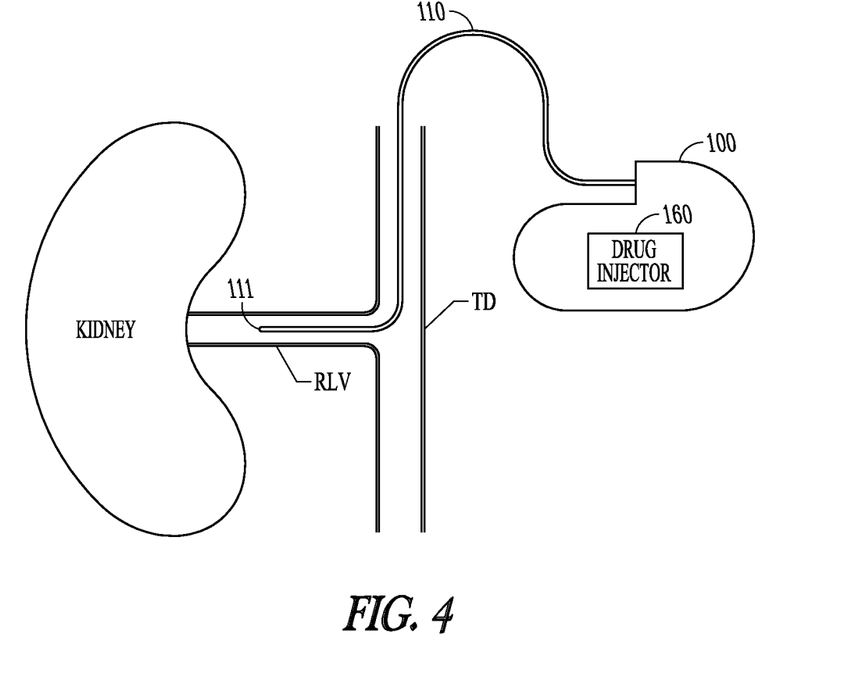
FIG. 4 shows an embodiment for delivering renal function modulation therapy by drug delivery via the lymphatic system.

FIG. 4 shows another embodiment in which the catheter 110 has a lumen that communicates from an opening 111 at the distal end of the catheter to a drug injector 160 in the implantable device 100. The implantable device 100 is then able to controllably deliver one or more selected medications that affect renal function directly to the kidney by injecting the medication through the lumen of the catheter and out the opening 111 so as to flow retrogradely through the renal lymphatic vessel to the kidney. Examples of drugs that could be delivered in this manner include morphine, diuretic agents, vasodilating or vasoconstricting agents, and agents that affect the production of renin.

Figure 5:
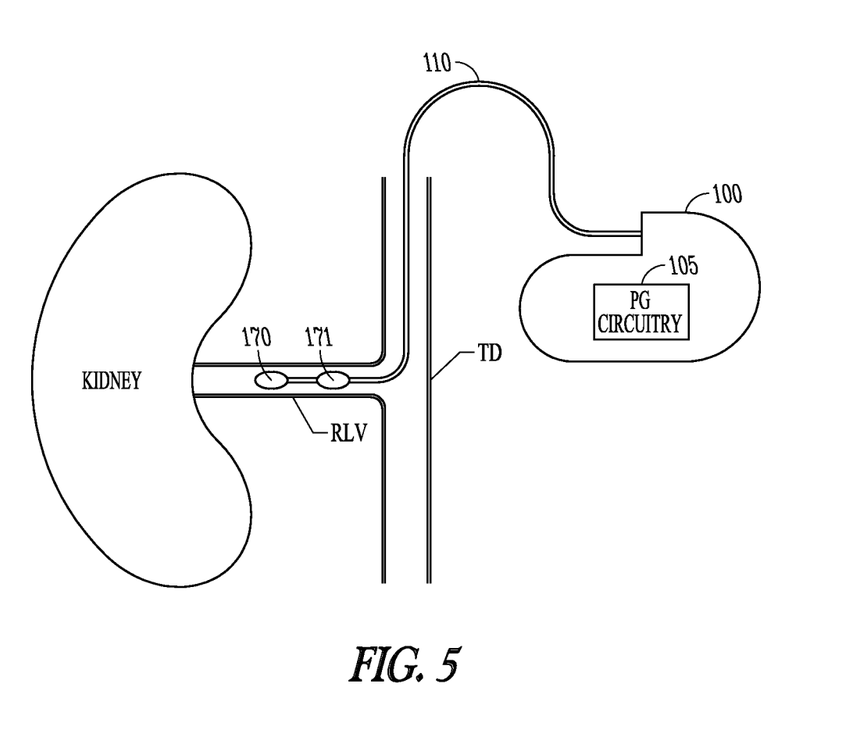
FIG. 5 shows an embodiment for delivering renal function modulation therapy by stimulation of the renal nerve.

FIG. 5 shows another embodiment in which a lead 110 from the implantable device 100 has a pair of electrodes 170 and 171 at its distal end. The lead 110 in this embodiment is disposed in the renal lymphatic vessel so that the electrodes are in proximity to the renal nerve. The electrodes 170 and 171 are connected to pulse generation circuitry 105 in the implantable device 100 so as to deliver electrical pulses to the renal nerve with selected amplitude, frequency, and polarity. In one embodiment, the implantable device may deliver depolarizing and/or hyperpolarizing neural stimulation pulses to the renal nerve in order to enhance and/or inhibit sympathetic activation of the kidney.

Figure 6:
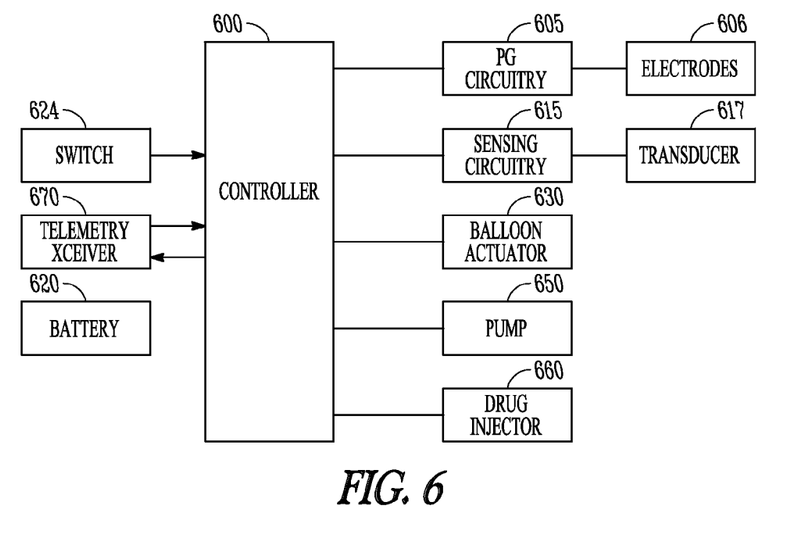
FIG. 6 is a system diagram of the functional components of an exemplary device for delivering renal function modulation therapy.

The embodiments of an implantable device for delivering renal function modulation therapy as described above may be used singly or in combination. For illustrative purposes, however, FIG. 6 is a system diagram of the functional components of an implantable device configured to deliver one or more of the renal function modulation therapies discussed above. A battery 620 provides power to the device. A programmable electronic controller 600 is interfaced to pulse generation circuitry 605 for controlling the output of neural stimulation pulses to the renal nerve as described above with reference to FIG. 5. Such neural stimulation pulses could also be delivered via intravascularly or endolymphatically disposed electrodes directly to an efferent parasympathetic nerve such as the vagus nerve or to an afferent nerve such as a baroreceptor (in the heart or pulmonary artery, for example) that causes parasympathetic stimulation and/or sympathetic inhibition via a reflex arc. The pulse generation circuitry 605 may be similar to that used in cardiac pacemakers and delivers electrical stimulation pulses to one or more neural stimulation electrodes 606. The electrodes may be bipolar or unipolar and may be integral to the unit housing or connected to the pulse generation circuitry by a lead. The pulse frequency, pulse width, pulse amplitude, pulse polarity, burst duration, and bipolar/unipolar stimulation configuration in this embodiment are programmable parameters, the optimal settings of which depend upon the stimulation site and the type and orientation of stimulation electrodes. The controller is also interfaced to a drug injector 660 for infusing a drug through a drug delivery catheter as described with reference to FIG. 4. The controller is also interfaced to a pumping mechanism 650 for augmenting lymphatic drainage from the kidney as described above with reference to FIG. 3. The controller is also interfaced with a balloon actuator 630 for supplying and withdrawing pressurized fluid from a balloon at the end of the catheter in order to controllably obstruct lymphatic flow from the kidney as described above with reference to FIG. 2.

The controller 600 may be made up of a microprocessor communicating with a memory, where the memory may comprise a ROM (read-only memory) for program storage and a RAM (random-access memory) for data storage. The controller could also be implemented by other types of logic circuitry (e.g., discrete components or programmable logic arrays) using a state machine type of design. As the term is used herein, the programming of the controller refers to either code executed by a microprocessor or to specific configurations of hardware components for performing particular functions. The controller includes circuitry for generating clock signals used to keep track of lapsed time intervals and deliver renal function modulation therapy in accordance with a defined duty cycle or schedule.

The controller is also interfaced to sensing circuitry 615 for sensing one or more physiological variables that may be used for closed-loop control of renal function modulation therapy. The sensing circuitry 615 is connected to one or more electrodes 617 or other types of transducers for sensing physiological variables affected by or otherwise related to renal function. In various embodiments, the sensing circuitry 615 and electrode 617 or other transducer may be a sensing channel for detecting cardiac electrical activity, a minute ventilation sensor, an accelerometer, a transthoracic impedance sensor, a chemosensor, or a pressure sensor. Examples of physiological variables that could be measured using these various sensing modalities include heart rate, heart rate variability, respiratory rate, activity level, blood oxygen concentration, blood electrolyte concentration, blood pH, blood osmolarity, cardiac output, and blood pressure.

The controller is also interfaced to an RF telemetry transceiver 670 that enables the device to communicate with an external programmer or other external device. The telemetry transceiver may also be used to wirelessly connect the implantable device to an external sensor such as for measuring blood pressure. Such an external blood pressure sensor may be, for example, a tonometric blood pressure sensor or a sphygmomanometer with telemetry capability. A magnetically or tactilely actuated switch 624 is also shown as interfaced to the controller to allow the patient to signal certain conditions or events to the implantable device. The switch 624 may be used, for example, to allow the patient to initiate and/or cease delivery of renal function modulation therapy.

Figure 7A:
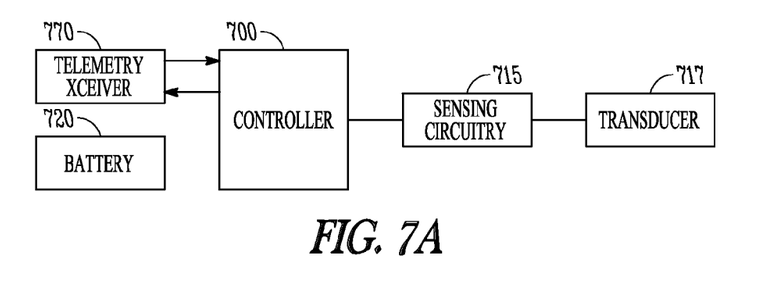
FIGS. 7A and 7B are system diagrams of exemplary satellite units.
Figure 7B:
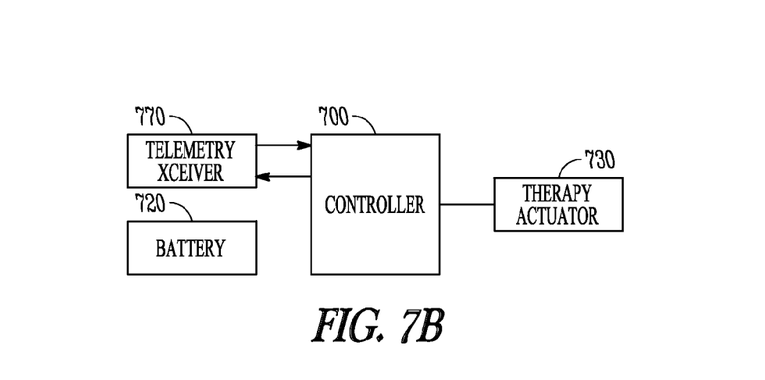

In other embodiments, the implantable device may use the telemetry transceiver 670 to communicate with one or more implantable satellite units that may incorporate any of the sensing and/or therapy modalities described above. Such embodiments may wirelessly communicate with a satellite unit for sensing and/or therapy delivery either in addition to or in place of sensing and/or therapy delivery components connected to the implantable device by means of a catheter or lead. FIG. 7A shows the system components of an exemplary satellite unit that includes a battery 720, a controller 700 interfaced to a telemetry transceiver 770, and sensing circuitry 715 which is connected to a transducer 717. FIG. 7B shows the system components of an exemplary satellite unit that includes a battery 720, a controller 700 interfaced to a telemetry transceiver 770, and a therapy actuator 730 which may be, for example, a pulse generator connected to electrodes, a drug injector, or an actuator for operating a mechanical structure for obstructing lymphatic flow.

As mentioned above, renal function modulation therapy may be delivered by an implantable device in either open-loop or closed-loop fashion. In the former case, commands to either initiate or cease one or more of the renal function modulation therapies may be issued via telemetry or by means of a patient actuated switch. In the latter case, one or more physiological variables are sensed by the implantable device and then used to control the delivery of the renal function modulation therapy. Because of the lag involved between the time such therapy is delivered and the time an effect on fluid balance is produced, it would normally be preferable to base control of renal function modulation therapy on one or more sensed variables as averaged over some specified period of time. Instantaneously measured values of certain physiological variables, however, could be used in some situations.

Figure 8:
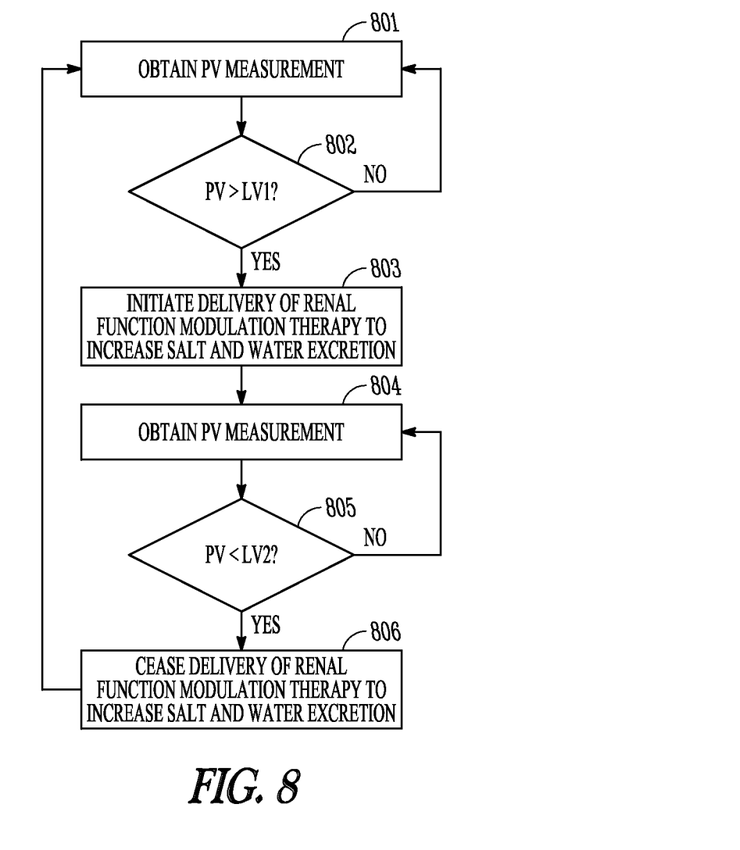
FIG. 8 illustrates an exemplary algorithm for delivering renal function modulation therapy in closed-loop fashion.

FIG. 8 shows an example of an algorithm that could be executed by the device controller in order to deliver renal function modulation therapy that increases the excretion of salt and water in response to a measured physiological variable PV. In the case of a hypertensive patient, for example, the variable PV could be blood pressure so that as blood pressure rises above a specified limit value LV1, the kidney is made to excrete more salt and water. Conversely, if the blood pressure falls below another specified limit value LV2, the blood pressure is deemed to be at an acceptable value so that renal function modulation can be withdrawn. In another example, a heart failure patient may be in some degree of compensation, and the variable PV could be cardiac output or a cardiac function index based upon a measured cardiac output and corresponding measured exertion level (e.g., heart rate, activity level, or minute ventilation). The cardiac function index could then be calculated to reflect the adequacy of cardiac output for a particular exertion level, so that if it is above the limit value LV1 it is deemed adequate and if it is below the limit value LV2 it is deemed inadequate. If it is supposed that the patient is overcompensated to some degree by the kidneys retaining more fluid than is necessary to produce adequate cardiac function, the algorithm could be used to make the kidneys excrete more salt and water as long as cardiac function is adequate as reflected by the cardiac function index. Referring to FIG. 8, at step 801, the device obtains a measurement of the variable PV. At step 802, the PV measurement is compared with a first limit value LV1. If the PV measurement is below the first limit value, the device returns to step 801 to continue measuring the variable PV. If the PV measurement rises above the first limit value, the device initiates delivery of renal function modulation therapy at step 803. Subsequently, at step 804, a PV measurement is again obtained. At step 805, the PV measurement is compared with a second limit value LV2. If the PV measurement falls below the second limit value, the delivery of renal function modulation therapy is ceased at step 806, and the device returns to step 801. Otherwise, the device continues to deliver renal function modulation therapy and monitor the variable PV at steps 804 and 805.

Delivery of renal function modulation therapy that decreases the excretion of salt and water may be similarly delivered in accordance with a measured physiological variable PV. The physiological variable PV may also represent measurement of a single variable or a composite function of a plurality of variables, measured as an average over some specified period of time or measured instantaneously. The physiological variable PV could also represent a particular condition such as the presence or absence of pulmonary edema as detected by a thoracic impedance sensor. In the case of a heart failure patient, for example, renal function modulation therapy could be initiated to increase excretion of salt and water when pulmonary edema is detected and ceased otherwise. Also rather than initiating and ceasing delivery of renal function modulation therapy in accordance with a variable PV, the amount of such therapy delivered could be controlled in closed-loop fashion in order to maintain the variable within a specified range by, for example, varying the extent and/or frequency of balloon inflation that obstructs renal lymph flow, varying the amount of fluid pumped from the renal lymphatic vessel that augments renal lymph flow, varying the amount of drug infused by a drug injector, or varying one or more parameters of the neurostimulation pulses delivered to the renal nerve in accordance with the measured variable PV. Titration of the amount of renal function modulation therapy could also be performed by varying a scheduled duty cycle for delivering such therapy in accordance with the variable PV.

It should be appreciated that the various embodiments described above may be used singly or combined in any manner considered to be advantageous. Those embodiments may also be combined with any of the methods or devices described in U.S. patent application Ser. No. 11/422,414, filed on Jun. 6, 2006, Ser. No. 11/422,417, filed on Jun. 6, 2006, now issued as U.S. Pat. No. 7,526,337, Ser. No. 11/422,418 filed on Jun. 6, 2006, now issued as U.S. Pat. No. 7,734,341, Ser. No. 11/559,131, filed on Nov. 13, 2006, Ser. No. 11/422,421, filed on Jun. 6, 2006, and Ser. No. 11/539,301, filed on Oct. 6, 2006, now issued as U.S. Pat. No. 7,664,548.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A device, comprising:
   a controller;
   pulse generation circuitry operable by the controller;
   one or more stimulation electrodes connected to the pulse generation circuitry adapted for endolymphatic disposition near the renal nerve; and
   wherein the controller is programmed to operate the pulse generation circuitry to deliver neural stimulation to the renal nerve.

2. The device of claim 1 wherein the neural stimulation inhibits sympathetic activation of the kidney.

3. The device of claim 1 wherein the neural stimulation enhances sympathetic activation of the kidney.

4. The device of claim 1 wherein the pulse generation circuitry delivers hyperpolarizing stimulation to the renal nerve.

5. The device of claim 1 wherein the pulse generation circuitry delivers depolarizing stimulation to the renal nerve.

6. The device of claim 1 further comprising:
   a drug injector operable by the controller; and,
   a drug delivery catheter connected to the drug injector and adapted for endolymphatic disposition near a kidney.

7. The device of claim 1 further comprising:
   a blood pressure sensor for providing a blood pressure measurement to the controller; and,
   wherein the controller is programmed to operate the pulse generation circuitry in closed-loop fashion in dependence upon the blood pressure measurement.

8. The device of claim 1 further comprising:
   a cardiac output sensor for providing a cardiac output measurement to the controller; and,
   wherein the controller is programmed to operate the pulse generation circuitry in closed-loop fashion in dependence upon the cardiac output measurement.

9. The device of claim 1 further comprising:
   an exertion level sensor;
   a cardiac output sensor; and,
   wherein the controller is programmed to compute a cardiac function index that reflects the adequacy of cardiac output for a particular exertion level and further programmed to operate the pulse generation circuitry in closed-loop fashion in dependence upon the computed cardiac function index.

10. The device of claim 1 further comprising:
    a transthoracic impedance sensor for detecting pulmonary edema; and
    wherein the controller is programmed to operate the pulse generation circuitry in closed-loop fashion in dependence upon the detection of pulmonary edema.

11. A method, comprising:
    introducing one or more stimulation electrodes into a renal lymphatic vessel near the renal nerve;
    connecting the stimulation electrodes to pulse generation circuitry operated by a controller;
    programming the controller to operate the pulse generation circuitry to deliver neural stimulation to the renal nerve.

12. The method of claim 11 wherein the neural stimulation inhibits sympathetic activation of the kidney.

13. The method of claim 11 wherein the neural stimulation enhances sympathetic activation of the kidney.

14. The method of claim 11 wherein the pulse generation circuitry delivers hyperpolarizing stimulation to the renal nerve.

15. The method of claim 11 wherein the pulse generation circuitry delivers depolarizing stimulation to the renal nerve.

16. The method of claim 11 further comprising:
    endolymphatically disposing a drug delivery catheter connected to a drug injector near a kidney; and
    operating the drug injector with the controller.

17. The method of claim 11 further comprising:
    providing a blood pressure measurement to the controller; and,
    programming the controller to operate the pulse generation circuitry in closed-loop fashion in dependence upon the blood pressure measurement.

18. The method of claim 11 further comprising:
    providing a cardiac output measurement to the controller; and,
    programming the controller to operate the pulse generation circuitry in closed-loop fashion in dependence upon the cardiac output measurement.

19. The method of claim 11 further comprising:
    an exertion level sensor;
    a cardiac output sensor; and,
    programming the controller to compute a cardiac function index that reflects the adequacy of cardiac output for a particular exertion level and further to operate the pulse generation circuitry in closed-loop fashion in dependence upon the computed cardiac function index.

20. The method of claim 11 further comprising:
    detecting pulmonary edema; and
    programming the controller to operate the pulse generation circuitry in closed-loop fashion in dependence upon the detection of pulmonary edema.

* * * * *